(12) United States Patent
Farber et al.

(10) Patent No.: US 7,180,014 B2
(45) Date of Patent: Feb. 20, 2007

(54) METHOD AND EQUIPMENT FOR AUTOMATED TRACKING AND IDENTIFICATION OF NONUNIFORM ITEMS

(76) Inventors: Boris Farber, 34461 Southside Park Dr., Solon, OH (US) 44139; Sofia Farber, 34461 Southside Park Dr., Solon, OH (US) 44139; Boris Lerner, 25333 Hilltop Dr., Beachwood, OH (US) 44122; Ellen Lerner, 25333 Hilltop Dr., Beachwood, OH (US) 44122

( * ) Notice: Subject to any disclaimer, the term of this patent is extended or adjusted under 35 U.S.C. 154(b) by 259 days.

(21) Appl. No.: 10/803,608

(22) Filed: Mar. 18, 2004

(65) Prior Publication Data

US 2004/0186683 A1   Sep. 23, 2004

Related U.S. Application Data

(60) Provisional application No. 60/456,251, filed on Mar. 20, 2003.

(51) Int. Cl.
*G01G 19/40* (2006.01)

(52) U.S. Cl. .......................... 177/25.19; 606/1
(58) Field of Classification Search ............ 177/25.19, 177/25.11–25.17, 50; 235/385; 604/318
See application file for complete search history.

(56) References Cited

U.S. PATENT DOCUMENTS

| | | | |
|---|---|---|---|
| 4,043,412 A | 8/1977 | Rock | |
| 4,157,738 A | 6/1979 | Nishiguchi et al. | |
| 4,219,089 A | 8/1980 | Gard et al. | |
| 4,229,420 A | 10/1980 | Smith et al. | |
| 4,342,391 A | 8/1982 | Schainholz | |
| 4,447,885 A | 5/1984 | Biss | |
| 4,493,384 A | 1/1985 | Yano et al. | |
| 4,629,016 A | 12/1986 | Knothe et al. | |
| 4,646,767 A | 3/1987 | Hikita | |
| 4,671,916 A | 6/1987 | Hamas | |
| 4,737,910 A | 4/1988 | Kimbrow | |
| 4,891,755 A * | 1/1990 | Asher | 705/28 |
| 4,943,939 A | 7/1990 | Hoover | |
| 5,374,813 A | 12/1994 | Shipp | |
| 5,573,529 A | 11/1996 | Haak et al. | |
| 5,608,193 A * | 3/1997 | Almogaibil | 177/25.13 |
| 5,610,811 A | 3/1997 | Honda | |
| 5,637,850 A | 6/1997 | Honda | |
| 5,650,596 A | 7/1997 | Morris et al. | |
| 5,923,001 A | 7/1999 | Morris et al. | |
| 5,991,728 A | 11/1999 | DeBusk et al. | |
| 5,995,937 A | 11/1999 | DeBusk et al. | |
| 6,223,137 B1 | 4/2001 | McCay et al. | |
| 6,384,349 B1 | 5/2002 | Voll | |
| 6,427,915 B1 * | 8/2002 | Wike et al. | 235/383 |
| 6,430,536 B2 | 8/2002 | Irving et al. | |

(Continued)

*Primary Examiner*—Randy W. Gibson
*Assistant Examiner*—Sean Kayes
(74) *Attorney, Agent, or Firm*—John D. Gugliotta (57) ABSTRACT

An apparatus comprising of a segmented instrument tray, precision scale, image processing system, photoelectric sensors and a Personal Computer (PC) is disclosed. Said apparatus provides an automated and accurate tracking of surgical instruments used during surgical operating procedure by counting and identifying a specific quantity and instrument type, which are removed from a sterilized instrument tray to be used during the procedure and subsequently returned to the tray upon procedure completion, thus preventing an accidental leaving of an instrument inside of a patient and significantly reducing time spent by the operation staff for the instrument accounting.

4 Claims, 5 Drawing Sheets

U.S. PATENT DOCUMENTS 6,581,204 B2 6/2003 DeBusk et al.
6,611,806 B1 8/2003 Harvey
6,617,530 B1 9/2003 Lin

* cited by examiner

METHOD AND EQUIPMENT FOR AUTOMATED TRACKING AND IDENTIFICATION OF NONUNIFORM ITEMS

RELATED APPLICATIONS

The present invention is a Continuation of, and was first described in, and claims the benefit of priority of U.S. Provisional Patent No. 60/456,251 filed on Mar. 20, 2003. There are no previously filed, nor currently any co-pending applications, anywhere in the world.

BACKGROUND OF THE INVENTION

1. Field of the Invention

The present invention relates generally to systems and methods used to automatically track and inventory nonuniform items in real-time, and more particularly to a method and equipment for automated tracking and identification of surgical instruments and consumables in a surgical operating room environment.

2. Description of the Related Art

Problems have long existing in maintaining an accurate accounting of tools, parts and components during many types of intricate procedures. These can relate from assembly and maintenance of aircraft engines, to general inventorying of non-uniform parts, and to keeping accurate track of surgical tools during medical procedures. In this last example, the loss of surgical instruments has been one of the major problems for most healthcare facilities for many years. This problem is particularly costly for large size hospitals comprising hundreds of operating rooms, and multimillion dollars of instrument inventory.

Instruments are lost during transfer from and to surgical processing departments, sterilization process and/or operating room procedures. But perhaps the most dangerous of all, they are lost inside the patients. Some studies indicate that surgical teams accidentally leave clamps, sponges and other tools inside about 1,500 patients nationwide each year.

There are several computerize solutions available on the market, which provides tracking of surgical instruments sets. Most systems use barcode-scanning technology to facilitate tracking of instruments through the decontamination process; the inspection assembly, and packaging process; and the sterilization cycle. These systems consider any particular set as a unit and provide list of the instruments comprising the set.

However, verification that set is actually complete is still done manually. Manual counts are performed in surgical processing departments after set assembly and upon return from operating room procedures. It is performed from two to four times by highly trained nurses before, during and after surgery. Manual count is not very reliable. It is destructive and stressful for operating team, open to counting mistakes, leading to multiple re-counts. Additionally, due to nationwide shortage of nurses, other personnel are often understaffed. Finally, and perhaps most importantly, this practice is very time consuming leading to underutilization of operating room resources.

A search of the prior art did not disclose any patents that read directly on the claims of the instant invention; however, the following references were considered related:

| U.S. Pat. No. | Inventor | Issue Date |
|---|---|---|
| 6,581,204 | DeBusk et al. | Jun. 17, 2003 |
| 6,430,536 | Irving et al. | Aug. 6, 2002 |
| 6,611,806 | Harvey | Aug. 26, 2003 |
| 5,573,529 | Haak et al. | Nov. 12, 1996 |
| 6,384,349 | Voll | May 7, 2002 |
| 6,617,530 | Lin | Sep. 9, 2003 |
| 5,650,593 | Morris et al. | Jul. 22, 1997 |
| 5,923,001 | Morris et al. | Jul. 13, 1999 |

Accordingly, there exists a need for a method and mechanism to automatically track and inventory nonuniform items in real-time.

SUMMARY OF THE INVENTION

It is therefore an object of the present invention to provide an improved method and apparatus to track and inventory a set of nonuniform items in real-time.

It is a feature of the present invention to provide a method and equipment that can be utilized for automated tracking and identification of surgical instruments in a surgical room environment.

Briefly described according to one exemplary embodiment of the present invention, a method of the instrument tracking involves preliminary (prior to sterilization) weighing of the individual instruments belonging to a standardized surgical instrument set and recording weight information in the computer file identifying the set. During a surgical procedure, sterilized instruments are placed on a segmented tray, with the instruments of a specific type being placed within the same segment. Tray is positioned on top of a precision scale. Image Analysis system detects placement or withdrawal of the instruments from a specific segment. Scale measures weigh difference prior to and after placement or withdrawal of any number of instruments from an individual segment. Signal from the scale and the Image Analysis system are collected by PC, and based on a weight differential and the specific segment position, computer program determines number and type of instruments inserted or withdrawn from the tray. For a consumables (sponges for example), scale and image processing system detect number of sponges removed from the sterilized area to be used during the surgical procedure, and photoelectric sensors detects disposal of the individual soiled sponges in the collection bag. Computer program provides visual and audible indication of the quantity and type of the instruments (or consumables) still remaining in the operating field.

An advantage of the present invention is that its teachings can be applied, within the scope of the present invention, to many different systems that require a real-time tracking of parts, tools, steps or components.

Advantages of the present invention, as applied to the exemplary embodiment, include increased real-time accounting accuracy of the location of surgical tools in a substantially diminished time span. Such advantages in this particular application are well known to provide numerous benefits associated with decreased surgical times.

Further, the present invention is anticipated as being capable of being adapted to many different complex systems utilizing a plurality of nonhomogeneous components, a plurality of specialized installation or assembly tools, a plurality of assembly systems, or any combination thereof.

BRIEF DESCRIPTION OF THE DRAWINGS

The advantages and features of the present invention will become better understood with reference to the following more detailed description and claims taken in conjunction with the accompanying drawings, in which like elements are identified with like symbols, and in which:

| DESCRIPTIVE KEY | |
|---|---|
| 10 | method and equipment for automated tracking and identification of surgical instruments in a surgical room environment |
| 15 | individual surgical instrument |
| 20 | complete standardized surgical instrument set |
| 25 | sterilization |
| 30 | accurate scale |
| 35 | computer data file |
| 40 | serial number |
| 45 | set completeness |
| 50 | setup process |
| 55 | operation phase |
| 60 | cleaning process |
| 65 | final verification phase |
| 70 | pictorial representation |
| 75 | computer monitor setup screen |
| 80 | instrument name field |
| 85 | set name data field |
| 90 | assembly instructions data field |
| 95 | instrument quantity data field |
| 100 | indication icons |
| 105 | platform |
| 110 | sterile cloth |
| 115 | segments |
| 120 | video camera |
| 125 | personal computer equipped with an image processing application |
| 130 | user |
| 135 | identifying bracelet |

-continued

| DESCRIPTIVE KEY | |
|---|---|
| 140 | consumables |
| 145 | disposal bag |
| 150 | thru beam detection system |
| 155 | multiple proximity detection system |
| 160 | first sensor |
| 165 | second sensor |
| 170 | computer monitor utilization screen |
| 175 | instrument quantity present data field |
| 180 | status icon |

DESCRIPTION OF THE PREFERRED EMBODIMENTS

The best mode for carrying out the invention is presented in terms of its preferred embodiment, herein depicted within the FIGS. 1 through 5.

1. Detailed Description of the Figures

Figure 1:
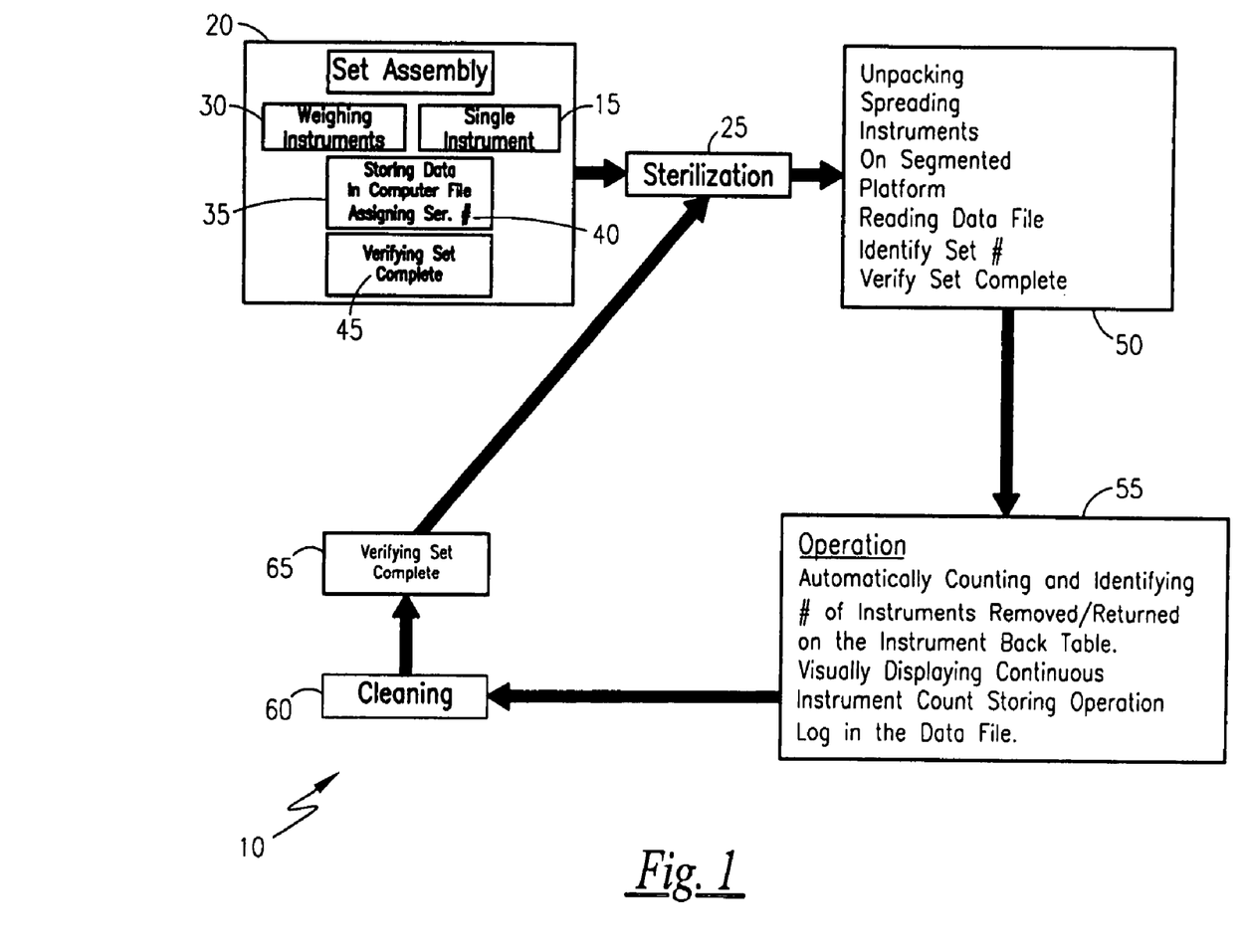
FIG. 1 is a logic diagram describing a method and equipment for automated tracking and identification of surgical instruments in a surgical room environment 10 according to the preferred embodiment of the present invention.

Referring now to FIG. 1, a logic diagram describing a method and equipment for automated tracking and identification of surgical instruments in a surgical room environment 10 according to the preferred embodiment of the present invention is disclosed. The weight of an individual surgical instrument 15 belonging to a complete standardized surgical instrument set 20 prior to sterilization 25 is measured with an accurate scale 30, envisioned to be accurate within ~0.1 g resolution. To simplify said procedure to form a complete standardized surgical instrument set 20 from individual surgical instrument 15, a picture of the individual surgical instrument 15 is displayed on a computer screen with the required number of instruments necessary for the set assembly as will be shown herein below. The individual surgical instrument 15 are placed on the accurate scale 30 one at a time according to screen request. Weights of the individual surgical instrument 15 are stored in a computer data file 35. A serial number 40 is assigned to the complete standardized surgical instrument set 20, which allows retrieval of information regarding instrument weights during operation. Set completeness 45 is automatically verified during set assembly, since the computer will automatically count and compare weights of measured pieces with nominal weights of this particular type of individual surgical instrument 15 stored in the database. However, it is further anticipated that in some situations it would be desired to provide an opportunity for single step verification for set completeness. Such a situation can be resolved by simply weighing the set and comparing its weight with the expected weight as stored in the computer date file 35. If no mismatch occurs, set completeness is verified. If a mismatch does occur, then the combinatoric algorithm defined in greater detail below can interactively point to potentially missing parts. In either case, during formation of the complete standardized surgical instrument set 20, a restriction is placed that weight of instruments of the same type cannot differ by more than two times (ratio between minimum and maximum weights of the same type instruments) to prevent rounding off error in the subsequent identification routine. After the sterilization 25, but prior to surgical procedure, sterilized instrument set is delivered to the operating room. Instruments are spread on a platform covered with a sterile cloth as defined by a setup process 50. Further description of the tracking process during an operation phase 55 will be defined herein below. At the conclusion of the operation phase 55, a cleaning process 60 occurs prior to a final verification phase 65, at which point the process would repeat starting with the sterilization 25, in the case of a repeated complete standardized surgical instrument set 20. To speed up final verification in the operating room, the present invention would anticipate the benefit of providing a second scale for used instruments for the instances where used, contaminated instruments are not returned to and in order to prevent cross contamination between sterile and non-sterile instruments.

Figure 2:
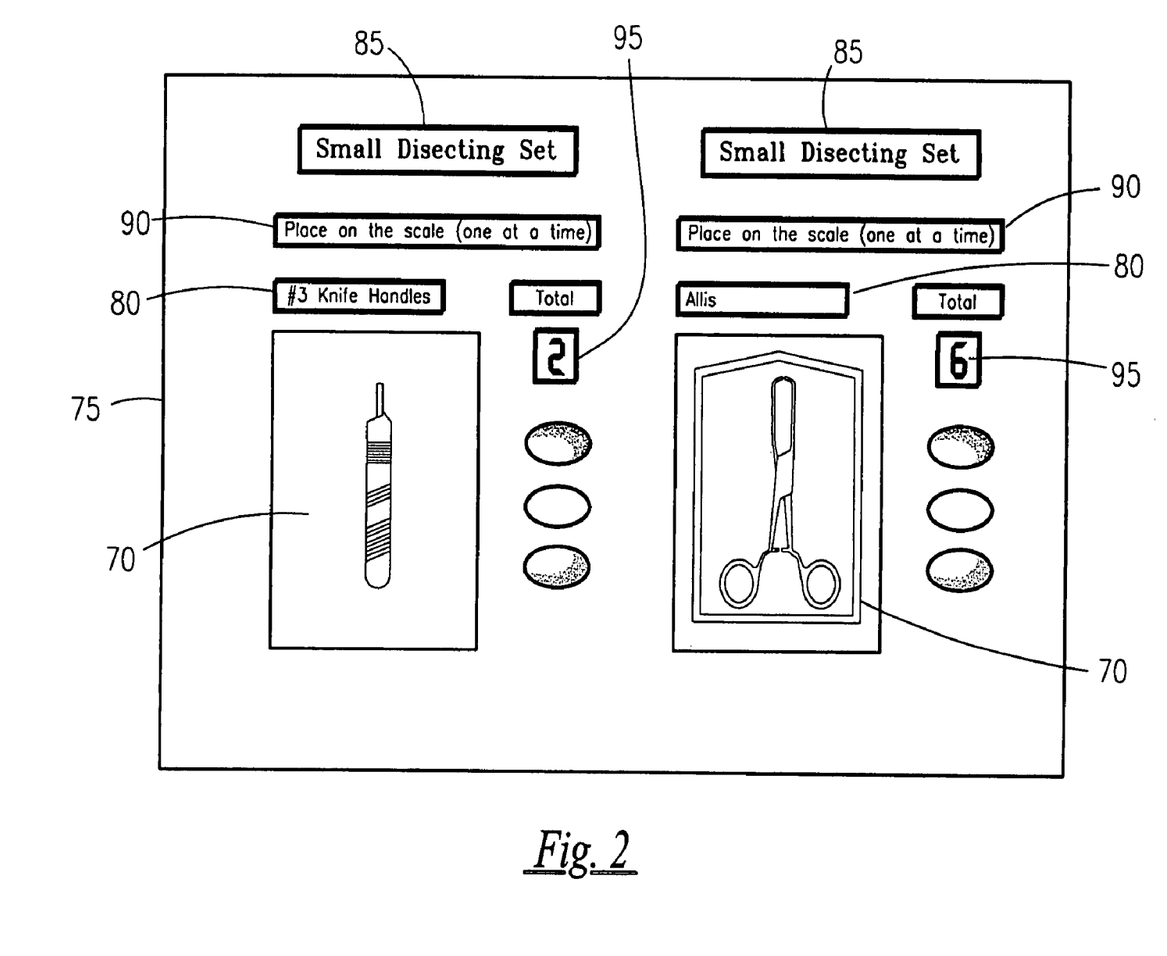
FIG. 2 is an example of an input screen on a computer during use of the method and equipment for automated tracking and identification of surgical instruments in a surgical room environment 10.

Referring now to FIG. 2, is an example of an input screen on a computer during use of the method and equipment for automated tracking and identification of surgical instruments in a surgical room environment 10 is shown. A pictorial representation 70 of each individual surgical instrument 15 (as seen in FIG. 1) is presented upon a computer monitor setup screen 75. Additional information such as the instrument name field 80 of each individual surgical instrument 15, as well as the set name data field 85 of the complete standardized surgical instrument set 20 (as seen in FIG. 1) being assembled is presented. An assembly instructions data field 90 is also provided to instruct the user on assembly of the complete standardized surgical instrument set 20, thus reducing training and errors. An instrument quantity data field 95 is provided to instruct the user on the specific quantity of the individual surgical instrument 15 needed in each complete standardized surgical instrument set 20. Finally, indication icons 100 are provided to alert the user of the respective status of the individual surgical instrument 15.

Figure 3A:
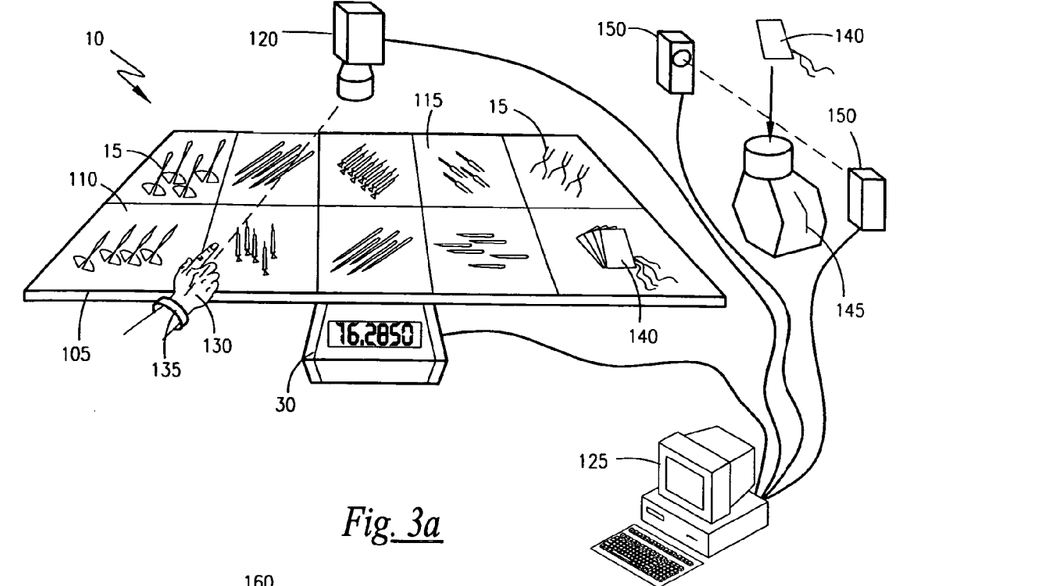
FIG. 3a is a block diagram of the method and equipment for automated tracking and identification of surgical instruments in a surgical room environment 10 utilizing an image processing system according to the preferred embodiment of the present invention.

Referring next to FIG. 3a, a block diagram of the method and equipment for automated tracking and identification of surgical instruments in a surgical room environment 10 utilizing an image processing system according to the preferred embodiment of the present invention is depicted. Individual surgical instrument 15 are spread on a platform 105 platform covered with a sterile cloth 110. The platform 105 is divided into segments 115 segmented, with the individual surgical instrument 15 of the same type being placed within the same segments 115. The platform 105 is positioned on top of the accurate scale 30. A video camera 120 is installed at some distance above the platform 105 or also known as the operating back-table. The video camera 120 is connected to a personal computer equipped with an image processing application 125. A user 130, such as a scrub nurse would wear an identifying bracelet 135 such as a color bracelet or a bracelet with a specific shape imprint on it with a color or imprint specifically chosen to differentiate it from the background. It can also be any identifiable mark or symbol on a cloth or surgical glove differentiating it from the background. The accurate scale 30 detects weight change above a specified level, envisioned to be greater than 0.1 grams. A signal is sent to the personal computer equipped with an image processing application 125 and from the acquired image, position of the hand of the user 130 which places or withdraws the individual surgical instrument 15 instruments from the segments 115 of the platform 105 can be identified by detecting the position of the identifying bracelet 135. Position of the hand of the user 130 provides a location of the segments 115 from which the individual surgical instrument 15 were withdrawn or placed. After the accurate scale 30 stabilizes, the personal computer equipped with an image processing application 125 will acquire a weight differential prior and after placement or withdrawal of the individual surgical instrument 15. Count of consumables 140, such as sponges, is accomplished by detecting new or sterile consumables 140 withdrawals by using abovementioned sequence for removal from the platform 105. Disposal of the soiled consumables 140 occurs in a disposal bag 145 and is monitored by use of a thru beam detection system 150, which counts individual soiled consumables 140 returned, with the aid of and a connection to the personal computer equipped with an image processing application 125. By adding up the weight of unused and used instruments and comparing it with the initial weight, verification of set completeness can be done in a single step. If there is a mismatch, the user can be guided to search for potentially missing parts, or used instruments can be returned and the system will automatically determine missing components.

Figure 3B:
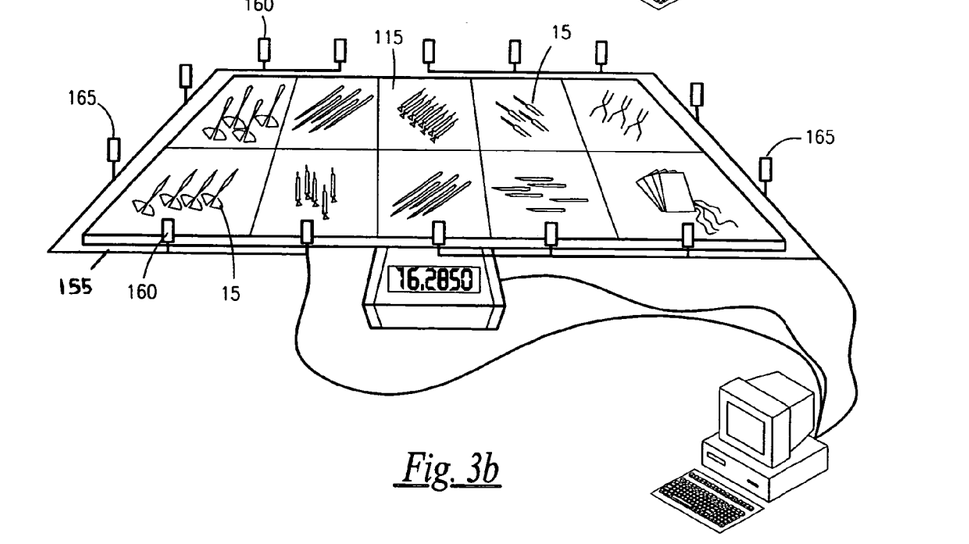
FIG. 3b is a block diagram of the method and equipment for automated tracking and identification of surgical instruments in a surgical room environment 10 utilizing multiple thru beam photoelectric sensors according to an alternate embodiment of the present invention.

Referring now to FIG. 3b, is a block diagram of the method and equipment for automated tracking and identification of surgical instruments in a surgical room environment 10 utilizing multiple thru beam sensors according to an alternate embodiment of the present invention is disclosed. Identification of the segments 115 where individual surgical instrument 15 were placed or removed can also be accomplished with any type of multiple proximity detection system 155, which are positioned in each segments 115 segment as shown. Every time, once a single or several individual surgical instrument 15 are placed or removed from the segments 115 on the platform 105, the segments 115 will generate a signal corresponding to a particular segment, where thru beam was interrupted. For example, as shown in this FIG., a first sensor 160 and a second sensor 165 will generate a signal, thus identifying a specific segment 115 with changed number of individual surgical instrument 15. Since instrument placement or withdrawal may potentially generate signals from several neighboring segments 115, a final verification procedure as described in FIG. 1 will be used. Should the segments 115 be comprised of ultrasonic proximity sensors, said sensors will identify hand position at the moments of scale disturbance, and verification procedure will be similar to the one described above.

Figure 4:
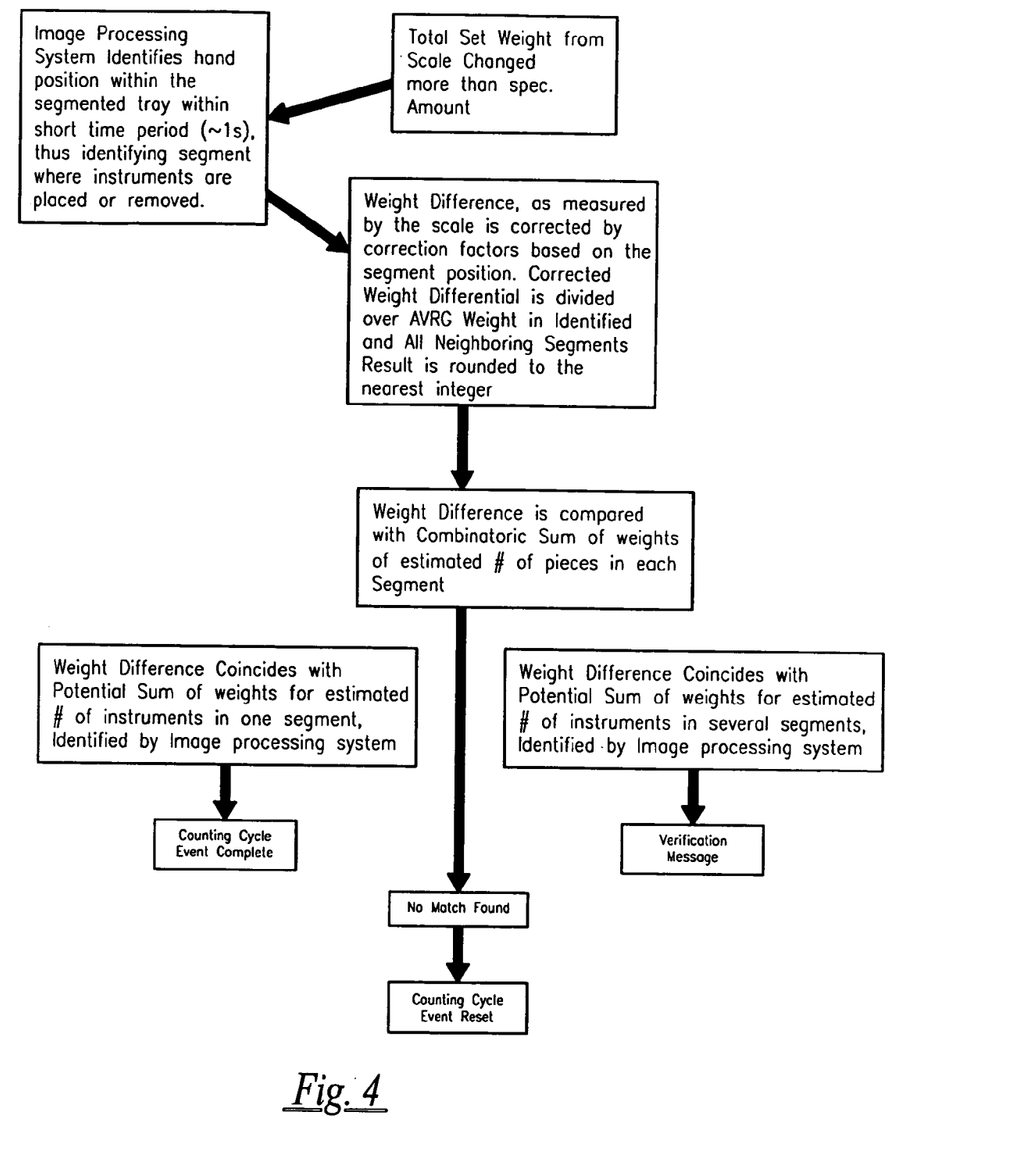
FIG. 4 is a logic diagram of the counting and identification method used by the image processing system as used with the method and equipment for automated tracking and identification of surgical instruments in a surgical room environment 10, and, FIG. 5 is a sample computer screen as used for automatic continuous counting of surgical instruments stored on the back table.

Referring next to FIG. 4, and using references from FIG. 3a, a logic diagram of the counting and identification method used by the image processing system as used with the method and equipment for automated tracking and identification of surgical instruments in a surgical room environment 10 is depicted. The personal computer equipped with an image processing application 125 determines average weight of the individual surgical instrument 15 placed within the same segments 115 based on the stored information according to the serial number 40 (as shown in FIG. 1) This average weight is defined by the formula:

$$X_j = \frac{\sum_{i=1}^{n} x_i}{n}$$

where, Xj is the average weight of the individual surgical instrument 15 placed in a segments 115 identified by number j. n is number of the instruments in segment j. It should be mentioned that relatively large segmented platform 105 placed on top of the accurate scale 30 could generate potential errors in weight determination, since the same individual surgical instrument 15 placed closer or further away from the center of the accurate scale 30 can produce slightly different scale readings. To eliminate these errors, correction factors are assigned to different segments, which will account for weight differentials vs. segment position relative to the scale center. Number of individual surgical instrument 15, which could have been potentially placed or removed from any segments 115, is determined by dividing corrected weight differential over average weight within an individual segment identified by the video camera 120 and the personal computer equipped with an image processing application 125. Result of the division (a fractional number) is rounded off to the nearest integer. As described above, during selection process, individual surgical instrument 15 of the similar type, which weights differ by more than two times are rejected from the set, thus preventing miscount due to rounding error.

To prevent misidentification, the following procedure is suggested. Since the personal computer equipped with an image processing application 125 provides only an approximate position of the segments 115, and each type of individual surgical instrument 15 within neighboring segments 115 can overlap, the number of individual surgical instrument 15, which could have been potentially removed from neighboring segments 115, is determined by dividing weight differential (prior and after scale stabilization) over average weight in neighboring segments 115 and rounding off to the nearest integer. To prevent wrong counts, based on the estimated number of pieces removed from each segments 115, combinatory sum of weights for the estimated number of individual surgical instrument 15 is determined in each segments 115 of interest. The combinatory sum is all possible combinations of weights of the estimated number of individual surgical instrument 15 positioned within the segments 115 of interest. If weight differential measured by the accurate scale 30 coincides with the estimated sum of the individual surgical instrument 15 weights in one of the segments 115, the number count and identification of the individual surgical instrument 15 is considered to be confirmed. If the above-described condition can be met for several neighboring segments 115, an audio and/or visual message will appear on the computer monitor requesting clarification of the counted number and types of the individual surgical instrument 15 placed or removed from the sterilized area. If no match can be found as which may occur in the case of an accidental disturbance of the accurate scale 30 the method and equipment for automated tracking and identification of surgical instruments in a surgical room environment 10 will be reset and total count of the individual surgical instrument 15 on the platform 105 will not be changed in this particular counting event.

Figure 5:
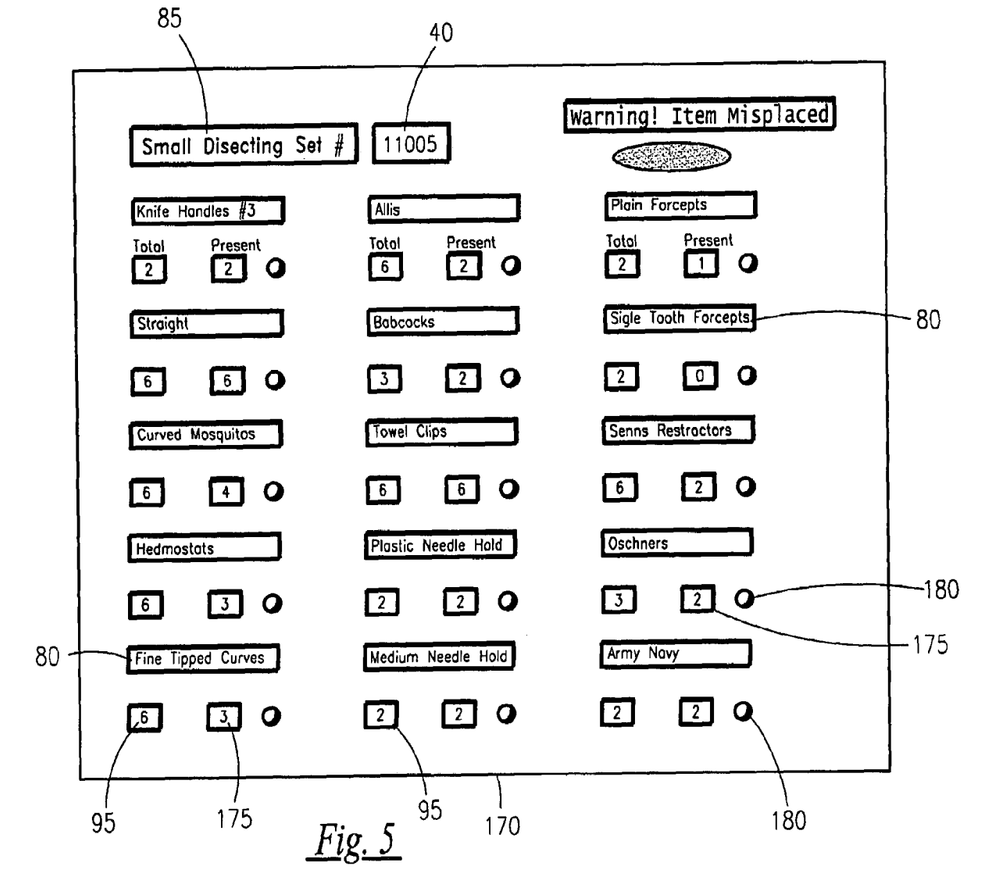

Referring finally to FIG. 5, a sample computer screen as used for automatic continuous counting of surgical instruments during operating room procedures is depicted. Count information is continuously displayed on a computer monitor utilization screen 170 as used in the operating room. Said screen will automatically update an instrument quantity present data field 175, dependent on verification procedure aforementioned described. Should the instrument quantity present data field 175 match the instrument quantity data field 95 as provided in the setup process 50 (as shown in FIG. 1), a status icon 180 will be colored as shown. Should said quantities not agree in number, the status icon 180 will be provided in another color. Such color coding, allows the user 130 (as shown in FIG. 3a) to instantly account for any and all individual surgical instrument 15 (as shown in FIG. 3a) Said individual surgical instrument 15 usage and history is tracked by the personal computer equipped with an image processing application 125, and should any individual surgical instrument 15 (as shown in FIG. 3a) change, a log file on the personal computer equipped with an image processing application 125 will be updated and stored with the identifying type and number of the individual surgical instrument 15 (as shown in FIG. 3a) which are placed or removed from the platform 105 (as shown in FIG. 3a) along with a time and date stamp reflecting the specific moment.

It is envisioned that other styles and configurations of the present invention can be easily incorporated into the teachings of the present invention, and only one particular configuration shall be shown and described for purposes of clarity and disclosure and not by way of limitation of scope.

2. Operation of the Preferred Embodiment

The preferred embodiment of the present invention can be utilized by the common user in a simple and effortless manner with little or no training. After installation of the method and equipment for automated tracking and identification of surgical instruments in a surgical room environment 10 in general accordance with either FIG. 3a or 3b, and installation of a personal computer equipped with an image processing application 125 configured with suitable programming to monitor described inputs and outputs, the method and equipment for automated tracking and identification of surgical instruments in a surgical room environment 10 is ready for use. Said use in an operating room environment will be generally identically to conventional operating room procedures and typically transparent to the user 130, with the exception of the addition of a computer monitor utilization screen 170 in the operating room.

The user 130 would place each individual surgical instrument 15 on the accurate scale 30 one at a time according to screen request. Weights of the individual surgical instrument 15 are stored in a computer data file 35, provided as part of the personal computer equipped with an image processing application 125. set completeness 45 is automatically verified during set assembly as part of the personal computer equipped with an image processing application 125. When complete, surgery proceeds in a conventional manner, and usage is tracked as described in FIG's. 3a, 3b and 4. At the conclusion of the operation phase 55, or surgery, the individual surgical instrument 15 would be cleaned in a cleaning process 60, and a final verification phase 65 occurs, which supports or replaces the conventional verification procedure. At this point the abovementioned process can repeat.

The foregoing descriptions of specific embodiments of the present invention have been presented for purposes of illustration and description. They are not intended to be exhaustive or to limit the invention to the precise forms disclosed, and obviously many modifications and variations are possible in light of the above teaching. It is anticipated that the teachings of the present invention, as exemplified by the present disclosure, can easily be applied or converted to any number of applications. The exemplary embodiments were chosen and described in order to best explain the principles of the invention and its practical application, to thereby enable others skilled in the art to best utilize the invention and various embodiments with various modifications as are suited to the particular use contemplated. It is intended that the scope of the invention be defined by the Claims appended hereto and their equivalents. Therefore, the scope of the invention is to be limited only by the following claims.

What is claimed is:

1. A method for automated tracking and identification of surgical instruments in a surgical room environment comprising:

f. Measuring the weight of individual surgical instruments belonging to a complete standardized surgical instrument set prior to sterilization by placing on a scale each said surgical instrument one at a time according to a prompt;

g. Storing the weights of the individual surgical instrument in a computer data file;

h. Assigning a serial number to the complete standardized surgical instrument set for allowing retrieval of information regarding instrument weights during an operation;

i. Automatically verifying set completeness during set assembly by the automatic counting and comparing of weights of measured pieces with nominal weights of this particular type of individual surgical instrument stored in a database;

j. If a mismatch occurs, then interactively pointing to potentially missing parts identified from said database, wherein said mismatch is identified by;

f. Placing a restriction that the weight of instruments of the same type cannot differ by more than two times (ratio between minimum and maximum weights of the same type instruments) to prevent rounding off error in any subsequent identification routine;

g. Identifying an instrument quantity to instruct the user on the specific quantity of the individual surgical instrument needed in each complete standardized surgical instrument set;

h Spreading individual surgical instruments on a platform divided into segments, with the individual surgical instrument of the same type being placed within the same segments and the platform weighed by a scale;

i Viewing said segmented platform by a video camera connected to a computer equipped with an image processing application;

j Placing upon a user an identifying indicia with a specific shape imprint on it with a color or imprint specifically chosen to differentiate it from the background;

k During removal of a surgical instrument, identifying a weight change above a specified level while signaling the computer equipped with said image processing application the position of the identifying indicia relative to the segmented platform during said weight change;

l Acquiring, by said computer equipped with an image processing application, a weight differential prior and after placement or withdrawal of the individual surgical instrument such as to be able to identify which instrument was removed from said platform;

wherein by adding up the weight of unused and used instruments and comparing it with the initial weight, verification of set completeness can be done in a single step.

2. The method of claim 1, wherein said identification subroutine comprises the steps:

a. Determining average weight of the individual surgical instrument placed within the same segments based on the stored information defined by the formula:

$$X_j = \frac{\sum_{i=1}^{n} x_i}{n}$$

where, Xj is the average weight of the individual surgical instrument placed in a segments identified by number j and n is number of the instruments in segment j;

b. Comparing the average weight to said weight differential; and c. Based on the estimated number of pieces removed from each segments, determining a combinatory sum of weights for the estimated number of individual surgical instrument determined in each segments of interest;

wherein said combinatory sum is all possible combinations of weights of the estimated number of individual surgical instrument positioned within the segments of interest.

3. The method of claim 2, wherein determining said combinatory sum comprises the steps:

a. Estimating the number of pieces placed or removed from said table by dividing the weight differential by the average weight in any particular segment;

b. Summing the estimated number of pieces for each segment;

c. Rounding the sum of the estimated number of pieces to the nearest integer; and d. Confirming the estimated integer by verifying equality of weight differential with the sum of the product of the average weight differential of the estimated number of pieces in the specific segment and surrounding segments.

4. A method for counting of surgical consumables comprising the steps:

a. detecting new or sterile consumables withdrawals the method of claim 1; and b. returning soiled consumables to a disposal bag monitored by use of a thru beam detection system which counts individual soiled consumables returned.

* * * * *